(12) United States Patent
Tam et al.

(10) Patent No.: US 8,840,931 B2
(45) Date of Patent: Sep. 23, 2014

(54) PHARMACEUTICAL COMPOSITIONS FOR DEHYDRATING, ATROPHYING AND ELIMINATING PATHOLOGICAL TISSUES

(76) Inventors: Kuok Leong Tam, Macao (CN); Io cheng Tam, Macao (CN); Hio man Tam, Macao (CN)

( * ) Notice: Subject to any disclaimer, the term of this patent is extended or adjusted under 35 U.S.C. 154(b) by 0 days.

(21) Appl. No.: 13/273,886

(22) Filed: Oct. 14, 2011

(65) Prior Publication Data
US 2012/0034316 A1   Feb. 9, 2012

Related U.S. Application Data

(63) Continuation-in-part of application No. 13/060,141, filed as application No. PCT/CN2009/073442 on Aug. 24, 2009, now abandoned.

(30) Foreign Application Priority Data

Aug. 22, 2008 (CN) .......................... 2008 1 0030331

(51) Int. Cl.
| | |
|---|---|
| *A61K 33/26* | (2006.01) |
| *A61K 33/04* | (2006.01) |
| *C01G 49/00* | (2006.01) |
| *A61K 31/245* | (2006.01) |
| *A61K 31/167* | (2006.01) |
| *A61K 47/06* | (2006.01) |
| *A61K 9/06* | (2006.01) |
| *A61L 26/00* | (2006.01) |
| *A61K 31/05* | (2006.01) |
| *A61K 9/00* | (2006.01) |
| *A61K 9/08* | (2006.01) |
| *A61K 47/10* | (2006.01) |
| *A61K 31/545* | (2006.01) |
| *A61K 9/12* | (2006.01) |
| *A61K 31/445* | (2006.01) |

(52) U.S. Cl.
CPC ............. *A61K 33/26* (2013.01); *A61L 2300/40* (2013.01); *A61K 31/245* (2013.01); *A61K 31/167* (2013.01); *A61K 47/06* (2013.01); *A61K 9/06* (2013.01); *A61L 26/0066* (2013.01); *A61K 31/05* (2013.01); *A61K 9/0014* (2013.01); *A61K 9/08* (2013.01); *A61K 47/10* (2013.01); *A61L 2300/102* (2013.01); *A61K 31/545* (2013.01); *A61K 9/0031* (2013.01); *A61K 9/12* (2013.01); *A61K 31/445* (2013.01); *A61K 9/0019* (2013.01)
USPC ........... 424/647; 424/709; 423/558; 423/326; 423/305; 423/700

(58) Field of Classification Search
None
See application file for complete search history.

(56) References Cited

U.S. PATENT DOCUMENTS

| | | | |
|---|---|---|---|
| 4,617,950 A | 10/1986 | Porteous et al. | |
| 5,011,693 A | 4/1991 | Whitefield | |
| 5,575,995 A | 11/1996 | Giovanoni | |
| 6,495,602 B1 * | 12/2002 | Bhagwat et al. | 514/588 |
| 6,652,840 B1 | 11/2003 | Prevendar | |
| 2006/0099161 A1 * | 5/2006 | Nakane et al. | 424/65 |
| 2006/0104920 A1 | 5/2006 | Allred | |
| 2009/0110645 A1 * | 4/2009 | Morelli et al. | 424/43 |

OTHER PUBLICATIONS

DermWeb, "Common types of topical formulations", Principles of Skin Therapy, Aug. 25, 2003, pp. 1-2. <http://web.archive.org/web/20030825162802/http://www.dermweb.com/therapy/common.htm>.*
wiseGEEK, "What is Menthol?", copyright 2003-2013, p. 1.<http://www.wisegeek.org/what-is-menthol.htm>.*
Merriam-Webster's Collegiate Dictionary, "Analogue", 10th edition, copyright 1996 by Merriam-Webster, Incorporated, p. 3.*
"Solid Polymer Ferric Silicate Sulphate (SPFSS)", Shaoyang Youhua Water Clarifying Material Co., Ltd., pp. 1-2, <http://www.youhuaspfs.com/p2-e.htm>, May 2006.*
International Search Report for international application No. PCT/CN2009/073442, dated Dec. 3, 2009 (5 pages).
Written Opinion for international application No. PCT/CN2009/073442, dated Dec. 3, 2009 (4 pages).
U.S. Appl. No. 13/060,141, filed Feb. 22, 2011 (12 pages).

* cited by examiner

*Primary Examiner* — Tracy Vivlemore
*Assistant Examiner* — Monica Shin
(74) *Attorney, Agent, or Firm* — Hamre, Schumann, Mueller & Larson, P.C.

(57) ABSTRACT

The present invention provides a pharmaceutical composition for dehydrating, atrophying and eliminating pathological tissues comprising inorganic polymeric ferric salt and/or inorganic polymeric ferric salt composite as its active ingredients, in which the inorganic polymeric ferric salt is polyferric sulfate, and the inorganic polymeric ferric salt composite is selected from a group consisting of poly-silicate ferric salts, polyphosphate ferric salts and their analogue. A surprising medical effect can be reached by treating pathological tissues with the pharmaceutical composition of the present invention which will make the treated pathological tissues dehydrated, atrophied, and absorbed or sloughed off. The pharmaceutical composition of the present invention is cost-effective, convenient to use and has significant effects in treatment of hemorrhoids, hemangiomas, varix, hygromas, abscess, tumors, scalding and burning wounds, bleeding traumatic wounds, and/or local injuries caused by chemical agents or microorganism.

8 Claims, 10 Drawing Sheets

Figure 2E:
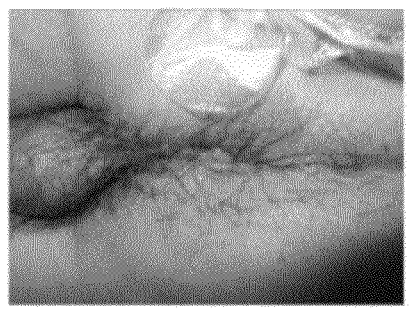

fig.1A
fig.1B
fig.2A
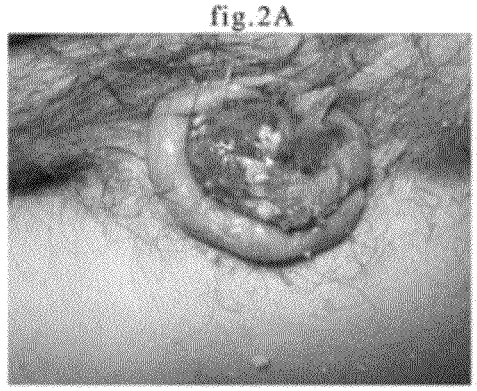
fig.2B
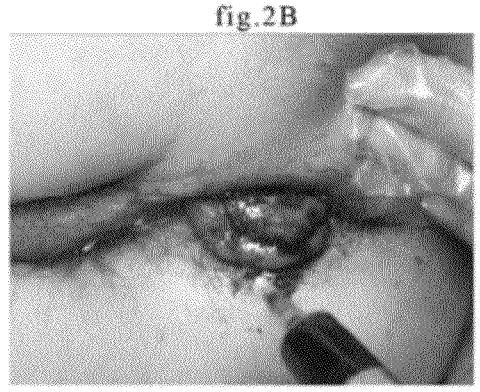
fig.2C
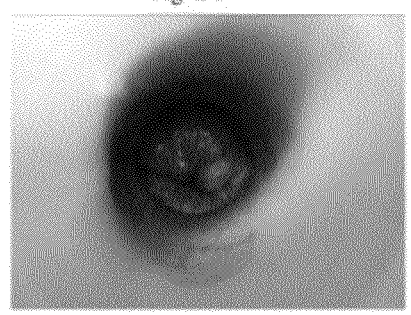
fig.2D
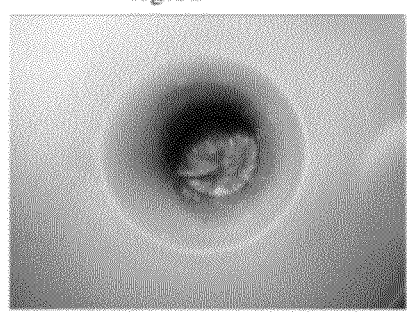

PHARMACEUTICAL COMPOSITIONS FOR DEHYDRATING, ATROPHYING AND ELIMINATING PATHOLOGICAL TISSUES

FIELD OF THE INVENTION

The present application is a continuation-in-part of U.S. application Ser. No. 13/060,141, filed Feb. 22, 2011, which is a national stage application of PCT/CN2009/073442, filed Aug. 24, 2009, which claims the benefit of priority from Chinese patent application number 200810030331.4, entitled "PHARMACEUTICAL COMPOSITIONS FOR DEHYDRATING, ATROPHYING AND ELIMINATING PATHOLOGICAL TISSUES" and filed in the name of Kuok Leong TAM on Aug. 22, 2008, its entire content is incorporated herein by reference.

BACKGROUND OF THE INVENTION

Polyferric sulfate (PFS) is a polymer made from ferric subsulfate, a compound having a molecular formula $Fe_4(OH)_2(SO_4)_5$. The molecular formula of polyferric sulfate is $[Fe_2(OH)_n(SO_4)_{3-n/2}]m$, where $0.5<n<1$ and $m=f(n)$.

Traditionally polyferric sulfate is used as inorganic flocculating agent. When compared with other kinds of flocculating agents polyferric sulfate has several advantages, such as relatively low dosage, adapt to be used in wide pH range, high removal ratio for impurities (turbidity, COD, suspended matters, etc.), low concentration of residues, high flocculating speed, good de-colorization effect, etc. At present polyferric sulfate is widely used for purifying treatment of industrial waste water, urban sewage, and domestic water. When polyferric sulfate is hydrolyzed in water it will produce polynuclear hydroxyl complex, which has a strong absorption for colloidal particles in a variety of water body and makes the particles aggregate and flocculate through bonding, bridging, and cross-linking.

In recent years, on the basis of flocculants such as polysilicate and poly-ferric sulfate, researchers developed the following new inorganic or organic polymer composite flocculants which contains polymeric ferric salt composite: polysilicate ferric composite salts, such as poly ferric silicate chloride (PFSC), polymeric ferric sulfate silicate (PFSS), and polysilicate ferric aluminum sulfate (PAFSC); polyphosphate ferric composite salts, such as polyphosphate ferric sulfate (PPFS); poly aluminum-ferric composite salts, such as polymeric aluminum ferric phosphate (PAFP); flocculants containing poly-ferric chloride sulfate (PFCS); flocculants containing co-polymeric ferric salts, such as poly-aluminum ferric chloride (PAFC); organic polymeric flocculants, such as organic cationic polymeric flocculants-DMC copolymer, CTS-AM-DMC strong cationic natural polmer (chitosan (CTS)-methacryloyl-oxyethyl trimethyl ammonium chloride (DMC)-acrylamide (AM) strong cationic natural polymer) flocculants and their analogue; organic/inorganic polymer composite flocculants, such as CAF (a kind of organic/inorganic polymer composite flocculants made from chitosan, polyaluminum, and ferric chloride) and its analogue.

Compared with ferric subsulfate and polyferric sulfate (PFS), the above mentioned new types of flocculants have higher molecular weights, stronger ability for adsorption and bonding, and better ability for removing turbidity, COD and BOD. For example, when treating sewage the dosage of polymeric ferric sulfate silicate (PFSS) is one-third less than that of polyferric sulfate. It was reported that when treating a slurry of coal, the dosing amount of an inorganic flocculants polyaluminum chloride is more than 1.0KG/per ton of coal when used alone, and the dosing amount of organic flocculants polyacrylamide is a bit less than 0.1KG/per ton of coal when used alone. However when both are used the dosing amount is much less due to their combination.

Although the use of the above substances as flocculants is well known up to the present no one has tried to make use of the properties of these substances in the medical field. That is to make pathological tissues in living bodies dehydrated, atrophied and eventually eliminated.

Therefore, there is a need to provide a novel pharmaceutical composition for dehydrating, atrophying and eliminating pathological tissues.

SUMMARY OF THE INVENTION

An object of the present invention is to provide a new effective pharmaceutical composition for dehydrating, atrophying and eliminating pathological tissues.

During their medical practice the inventors of the present invention surprisingly discovered that when inorganic polymeric ferric salt and/or inorganic polymeric ferric salt composite as flocculants are used in the medical field they made pathological tissues dehydrated, atrophied, and eventually eliminated. For example, polyferric sulfate, polymeric ferric sulfate silicate (PFSS), polyferric silicate chloride (PFSC), and polyphosphate ferric sulfate (PPFS) would make the pathological tissues of human bodies who suffered from local diseases or wounds dehydrated, atrophied, and eventually eliminated. These kinds of flocculants can be used in the medical field to treat hemorrhoids, hemangiomas, varix, hygromas, abscess, tumors, scalding and burning wounds, bleeding traumatic wounds, and/or local injuries caused by chemical agents or microorganism, and make pathological tissues dehydrated, atrophied, and eliminated, which will finally cure the patients.

The inventors of the present invention discovered that when flocculants such as ferric subsulfate were used to treat bleeding wounds for hemostasis the formation of black solid particulate matter was observed in form of precipitation, and clear and transparent was isolated. The inventors determined that the mechanism of this phenomenon was the dehydration, atrophy, and elimination of blood and blood tissues, rather than the well-known mechanism of an astringent of Monsell in the literature in which hemostasis was caused by forming a thrombus of blood platelet and fibrin, aggregation of erythrocyte, and accelerated coagulation of blood.

In the medical field many diseases are caused by pathological changes of local tissues, such as hemorrhoids, hemangiomas (hemangiomas on or in skin, anus, liver, cerebrum, etc), varix of lower limb, intracranial hematoma, lymphangioma, hygromas, abscess, some tumors, scalding and burning wounds, bleeding traumatic wounds, and/or local injuries caused by chemical agents or microorganism, etc. The symptoms of these diseases are abnormally hyperplasia, congestion, hyperaemia, hemorrhage, hydropsy, inflammation, exudation, and necrosis of the pathological tissues which have an abnormal and contaminated biological colloidal solution like those sewage from the natural environmental or from industrial application.

Therefore the present invention provides a pharmaceutical composition for dehydrating, atrophying and eliminating pathological tissues, comprising inorganic polymeric ferric salt and/or inorganic polymeric ferric salt composite as its active ingredients. The inorganic polymeric ferric salt is polyferric sulfate, and the inorganic polymeric ferric salt composite is selected from a group consisting of poly-silicate ferric salts, polyphosphate ferric salts and their analogue.

Preferably the poly-silicate ferric salts in the pharmaceutical composition are polymeric ferric sulfate silicate (PFSS) and/or polyferric silicate chloride (PFSC), and the polyphosphate ferric salts are polyphosphate ferric sulfate (PPFS).

The preparation of the pharmaceutical composition is in form of a solid powder preparation, a paste preparation, a powder injection preparation, an aqua preparation, an injection preparation, a liniment preparation for external application, a suppository preparation, or a spray preparation.

Preferably the pharmaceutical composition in the present invention further comprises anesthetic, especially local anesthetic. For example the pharmaceutical composition in the present invention comprises one or more anesthetic selected from a group consisting of levobupivacaine, ropivacaine, lidocaine hydrochloride, menthol, methylene blue, procaine and tetracaine.

In one embodiment of the present invention, the pharmaceutical composition is a solid powder preparation which contains 1~60 wt. %, preferably 5~60 wt. %, more preferably 10~50 wt. % of inorganic polymeric ferric salt and/or inorganic polymeric ferric salt composite, adequate amount of anesthetic, and balanced amount of pharmaceutically acceptable solid excipient.

In another embodiment of the present invention, the pharmaceutical composition is a solid powder preparation which contains 1~60 wt. %, preferably 5~60 wt. %, more preferably 10~50 wt. % of inorganic polymeric ferric salt and/or inorganic polymeric ferric salt composite, 40~80 wt. % of zeolite powder, and balanced amount of other pharmaceutically acceptable solid excipient.

In still another embodiment of the present invention, the pharmaceutical composition is a paste preparation which contains 1~60 wt %, preferably 5~60 wt. %, more preferably 10~50 wt. % of inorganic polymeric ferric salt and/or inorganic polymeric ferric salt composite, adequate amount of anesthetic, and balanced amount of pharmaceutically acceptable excipient.

In yet another embodiment of the present invention, the pharmaceutical composition is an aqua preparation which contains 0.2~60 wt. %, preferably 1~60 wt. %, more preferably 5~60 wt. % of inorganic polymeric ferric salt and/or inorganic polymeric ferric salt composite, adequate amount of anesthetic, and balanced amount of water. For example, the pharmaceutical composition in the present invention can be first prepared into a powder injection preparation, and then prepared into an aqua with a concentration of more than 0.2% for local injection of pathological tissues when in clinical use.

As another aspect of the present invention it provides a usage of the above pharmaceutical composition for production of a medicine for dehydrating, atrophying and eliminating pathological tissues. For example the usage is for production of a medicine to treat hemorrhoids, hemangiomas, varix, hygromas, abscess, tumors, scalding and burning wounds, bleeding traumatic wounds, and/or local injuries caused by chemical agents or microorganism.

The inventors of the present invention employed inorganic polymeric ferric salt and/or inorganic polymeric ferric salt composite, which are traditionally used as water treatment agents, to treat pathological tissues for their dehydrating and atrophying. The treated pathological tissues are subsequently absorbed by, or slough from normal tissues. The effects for depressing pathological tissues by the pharmaceutical composition of the present invention are totally surprising. The pharmaceutical composition of the present invention are cost-effective, convenient to use and have significant effects in treatment of vascular diseases such as hemorrhoids, hemangiomas, hematomas (including hematomas caused by brain hemorrhage), thrombi and varix, and topical traumas such as bleeding and edemas. The compositions are also capable of killing various tumor cells by targeted injection.

The present invention will be further explained in details in connection with the following examples. Based upon its first discovery of the medical use of inorganic polymeric ferric salt and/or inorganic polymeric ferric salt composite the present invention is not limited to the preparation forms and ingredient ratios of these examples described herein. Any pharmaceutical composition comprising inorganic polymeric ferric salt and/or inorganic polymeric ferric salt composite as active component to dehydrate and atrophy pathological tissues in the medical field or any usage of such a pharmaceutical composition belong to the protection scope of the present invention.

BRIEF DESCRIPTION OF ATTACHED FIGURES

FIGS. 1-12 are photos taken from different patients to demonstrate the medical effects when treated by the pharmaceutical composition according to the present invention.

PREFERRED EMBODIMENTS OF THE INVENTION

In-vitro Experiments

The inventors of the present invention employed inorganic polymeric ferric salt, i.e. polyferric sulfate, which has a greater molecular weight than ferric subsulfate, to perform in-vitro experiments with different kinds of human blood, i.e. un-coagulated blood without anticoagulant, un-coagulated blood with anticoagulant, and natural cruor. The experiments demonstrated that all kinds of blood would flocculate and dehydrate without any exception. The ratio for complete reaction was about 2 ml of human blood to 0.4 ml of 10 wt. % polyferric sulfate solution, observing from these experiments. This datum could be taken as potency ratio of polyferric sulfate, which means the relative concentration or dosing amount for equivalent effect. As a safer and more preferable embodiment the inventors recommended that the volume ratio of 5 wt. % polyferric sulfate to pathological tissues is 1:3. Similarly, the potency ratios for dehydrating and atrophying pathological tissues of the pharmaceutical composition of the present invention, as well as preferred embodiments for clinical use, could be determined by in-vitro experiments.

The following tables summarized the procedures and results for the in-vitro experiments of polyferric sulfate, in which table I demonstrated the in-vitro experiments of polyferric sulfate for dehydrating human blood and the corresponding results, and table II demonstrated the in-vitro reaction of polyferric sulfate in low concentration with human blood, i.e. dehydration.

TABLE I

In vitro experiments and results of dehydration effect of polyferric sulfate on blood

| Groups | I | II | III | IV | V |
|---|---|---|---|---|---|
| Processes and Results | A. 0.2 ml of 3.8% sodium citrate; B. adding 2 ml of human blood; C. fully mixing A and B for 3 minutes to form a anti-coagulated mixture; D. adding 0.2 ml of 10% polyferric sulfate, and stirring, in which coagulation and precipitation were observed in 10 seconds, and after 5 min. a small amount of blood still un-reacted; E. after 30 min. further adding 0.2 ml of 10% polyferric sulfate to achieve a complete reaction: 1. The precipitate was a black and solid powder, particle or bulk; 2. Red color (blood) disappeared; 3. Colorless and transparent water was isolated. | A. 0.2 ml of 1:10000 aspirin; B. adding 2 ml of human blood; C. fully mixing A and B for 3 minutes to form a anti-coagulated mixture; D. adding 0.2 ml of 10% polyferric sulfate, and stirring, in which coagulation and precipitation were observed in 5 seconds, after 5 min. a small amount of blood still un-reacted; E. after 30 min. further adding 0.2 ml of 10% polyferric sulfate to achieve a complete reaction: 1. The precipitate was a black and solid powder, particle or bulk; 2. Red color (blood) disappeared; 3. Colorless and transparent water was isolated. | A. 2 ml of uncoagulated fresh human blood; B. adding 0.2 ml of 10% polyferric sulfate, and stirring, in which coagulation and precipitation were observed in 10 seconds, after 5 min. 1 a small amount of blood still un-reacted; C. after 30 min. further adding 0.2 ml of 10% polyferric sulfate to achieve a complete reaction: 1. The precipitate was a black and solid powder, particle or bulk; 2. Red color (blood) disappeared; 3. Colorless and transparent water was isolated. | A. 2 ml of self-coagulated human blood taken from body 10 min before; B. after 30 min., the above human blood separated into layers with the supernate being serum; C. adding 0.2 ml of 10% polyferric sulfate at min. 50, and then black particles were observed under the serum 2 min. later with colorless and transparent liquid surrounded (isolated water?); D. further adding 0.2 ml of 10% polyferric sulfate at 70 min. to achieve a complete reaction: 1. The precipitate was a black and solid powder, particle or bulk; 2. Red color (blood) disappeared; 3. Colorless and transparent water was isolated. | A. adding 0.2 ml of 3.8% sodium citrate to 2 ml of human blood for anti-coagulating 30 min; B. adding 0.4 ml of 10% polyferric sulfate at min. 65 and stirring; C. observing coagulation and precipitation in 5 seconds, and reactions being completed in 1 min.: 1. The precipitate was a black and solid powder, particle or bulk; 2. Red color (blood) disappeared; 3. Colorless and transparent water was isolated. |
| Conclusions and ions | A. Reactions between polyferric sulfate and human bloods are flocculation, precipitation and dehydration; B. Sodium citrate as anticoagulant reactions; C. Suitable ratio for complete reaction is; 2 ml human blood: 0.4 ml 10% polyferric sulfate (i.e., 5:1) D. Conclusion: polyferric sulfate solution can be used for topical hemostasis of the patients suffering from coagulation disability being administrated with anticoagulants. E.g, it can be used for surgical bleedings, traumatic bleeding or other bleedings such as brain hemorrhage, subdural hemorrhage, extradural hemorrhage. Hemophilia hemorrhage, etc. | A. Same as Left A; B. Aspirin as anticoagulant has no effect on the above reactions; C. Same as Left C; D. Same as Left D; Complete reaction is obtained at a ratio of 1.5 = 10% polyferric sulfate human blood: dehydration and atrophying in 10 min., and tissue sloughing in 5-7 days | A. Same as Left A; B. Same as Left C; Same experiments can be made by 10% polyferric sulfate and 2% lydocain 1.5 = 10% polyferric sulfate human blood | A. Same as Left A; B. Same as Left C; C. 10% polyferric sulfate can flocculate, precipitate and dehydrate blood and dissolve self-coagulated blood clot (thrombi or hematomas). Therefore, polyferric sulfate can be used to treat thrombosed external hemorrhead, cirsoid thrombi, brain hemorrhage, and coagulated hematomas of subdural hemorrhage by dissolving blood clot of thrombi. | A. Same as Left A; B. 1 part of 3.8% sodium citrate mixed with 9 parts of human blood has anticoagulation effect; C. Same as the D in Group I. 1.10 = 0.2 ml 10% polyferric sulfate 2 ml human blood. For complete reaction 1.5 = 0.4 ml 10% polyferric sulfate 2 ml human blood |

TABLE II

In vitro experiments of polyferric sulfate in low concentration

| Groups | 1 | 2 | 3 |
|---|---|---|---|
| Contents | 0.2 ml 5% polyferric sulfate, and 2 ml human blood (1:10) | 0.4 ml 5% polyferric sulfate; and 2 ml human blood (1:5) | 1 ml coagulated human blood; and 0.2 ml 5% polyferric sulfate |
| Results 1 24 h | Significant black precipitates and water observed after 2 minutes; Reaction completed in 20 minutes; and Residual in red color of blood (++) (observing for 24 h) | Significant black precipitates and water observed after 2 minutes; Reaction completed in 20 minutes; and Residual in red color of blood (+) (observing for 24 h) | Significant black precipitates and water observed after 2 minutes; Reaction completed in 20 minutes; and Residual in red color of blood (+) (observing for 24 h) |
| Results 2 48 h | Residual in red color of blood (+); and Nottotally coagulating | Residual in red color of blood (+−); and Nottotally coagulating | Residual in red color of blood (+−); and Nottotally coagulating |
| Results 3 72 h | Same as above | Residual in red color of blood (+−); and Nottotally coagulating | Same as above |
| Conclusions | Underreaction | Reaction is near to being complete, 5% polyferric sulfate is recommended as safe and optimal embodiment, and recommended clinical dosage is 1:3 | 1. Same as left; 2. Coagulated blood can be dissolved |

The inventors observed in other experiments that inorganic polymeric ferric salts, such as polyferric sulfate, and inorganic polymeric ferric salt composite, such as polymeric ferric sulfate silicate (PFSS), polyferric silicate chloride (PFSC) and polyphosphate ferric sulfate (PPFS), showed a strong flocculation and dehydration for human blood, while polymeric aluminum salts, such as polyaluminum chloride and polyaluminum sulfate, and organic polymeric flocculants, such as polyacrylamide, did not show dehydration for human blood. If these two kinds of substances were mixed together the dehydration from inorganic polymeric ferric slats would be reduced or even be eliminated.

PREPARATION AND APPLICATION OF PHARMACEUTICAL COMPOSITION

Example 1

10 grams of polyferric sulfate are dissolved in 90 grams of distilled water. The obtained solution is distributed into bacteria-free ampoules in size of 3 ml, evacuated, and melting sealed. Dilute it with equal volume injection comprising 1.5 wt. % levobupivacaine and 1 wt. % methylene blue, and obtain an injection comprising 5 wt. % polyferric sulfate, 0.75 wt. % levobupivacaine and 0.5 wt. % methylene blue. Treat various hemorrhoids, hemangiomas, varix and bleeding hematomas with it in an adequate amount.

The injection procedure comprises steps of cleaning and sterilizing the affected parts; injecting the solution into the hemorrhoids, hemangiomas, hematomas or thrombi at several points; and pressing the affected parts with cotton swab to evenly distribute the solution with the hemorrhoids, hemangiomas or thrombi becoming stiff within seconds. The hemangiomas and hematomas began to soften, dehydrate, atrophy and disappear after three minutes or more. The dehydration and atrophying process completed within ten to twenty minutes. After seven to fourteen days, the pathological tissues were either substituted by normal tissues or sloughed, and the wounds were cured. No co-effect, bleeding, scar or any other side effect was observed. Therefore, this method is a novel dehydration therapy for hemorrhoids, hemangiomas, hematomas, and thrombi. The pharmaceutical compositions have very specific, rapid and excellent effect in dehydration and atrophying of the blood stasis pathological tissues caused by the varix, hematomas and thrombi in hemorrhoids, which was not found in any literatures worldwide.

Example 2

7 grams of polymeric ferric sulfate silicate (PFSS) are dissolved in 93 grams of distilled water, and then distributed into bacteria-free ampoules in size of 3 ml, evacuated, and melting sealed. Dilute it with equal volume injection comprising 1.5 wt. % levobupivacaine and 1 wt. % methylene blue, and obtain an injection comprising 3.5 wt. % polyferric sulfate, 0.75 wt. % levobupivacaine and 0.5 wt. % methylene blue. Treat various hemorrhoids, hemangiomas, varix and bleeding hematomas with it in an adequate amount.

Example 3

7 grams of polyferric silicate chloride (PFSC) are dissolved in 93 grams of distilled water, and then distributed into bacteria-free ampoules in size of 3 ml, evacuated, and melting sealed. Dilute it with equal volume injection comprising 1.5 wt. % levobupivacaine and 1 wt. % methylene blue, and obtain an injection comprising 3.5 wt. % polyferric sulfate, 0.75 wt. % levobupivacaine and 0.5 wt. % methylene blue. Treat various hemorrhoids, hemangiomas, varix and bleeding hematomas with it in an adequate amount.

Example 4

7 grams of polyphosphate ferric sulfate (PPFS) are dissolved in 93 grams of distilled water, and then distributed into bacteria-free ampoules in size of 3 ml, evacuated, and melting sealed. Dilute it with equal volume injection comprising 1.5 wt. % levobupivacaine and 1 wt. % methylene blue, and obtain an injection comprising 3.5 wt. % polyferric sulfate, 0.75 wt. % levobupivacaine and 0.5 wt. % methylene blue. Treat various hemorrhoids, hemangiomas, varix and bleeding hematomas with it in an adequate amount.

Example 5

10 grams solid powder of polyferric sulfate are mixed with 90 grams of Vaseline oil, 1 gram of menthol, and 0.75 gram of levobupivacaine to form a soft paste. The soft paste is distributed into plastic soft tubes with 10 grams/tube, and sealed for clinical use. Apply the soft paste onto traumatic wounds, scalding and burning wounds, local injuries caused by chemical agents or cytotoxins, infective wounds by bacteria or virus, or vomicae after removing pus. Such a treatment can reach the effects of cleaning, removing pus, killing bacteria and virus, detoxicating, staunching, apocatastasis, desiccating, scabbing, and promoting healing.

Example 6

10 grams of solid powder of polyferric sulfate, 0.25 gram of menthol and 0.75 gram of levobupivacaine are dissolved in 90 grams of distilled water, filtered by a bacteria filter, distributed into bacteria-free brown glass bottles or plastic bottles in size of 100 ml, 250 ml or 500 ml, and sealed for clinical use. Treat traumatic wounds, infective and inflammatory wounds, vomicae after removing pus, and local injuries caused by chemical agents or cytotoxins by spraying or embrocating. Such a treatment can reach the effects of cleaning, removing pus, staunching, apocatastasis, killing bacteria and virus, detoxicating, and promoting healing.

Example 7

5 grams of solid powder of polyferric sulfate, 0.25 gram of menthol or mint and 0.75 gram of levobupivacaine are dissolved in 94 grams of distilled water, filtered by a bacteria filter, distributed into bacteria-free brown glass bottles or plastic bottles in size of 100 ml, 250 ml or 500 ml, and sealed for clinical use. Treat traumatic wounds, infective and inflammatory wounds, vomicae after removing pus, and local injuries caused by chemical agents or cytotoxins by spraying or embrocating. Such a treatment can reach the effects of cleaning, removing pus, staunching, apocatastasis, killing bacteria and virus, detoxicating, and promoting healing.

CLINICAL EXPERIMENT OBSERVATIONS

Ferric subsulfate, inorganic polymeric ferric salt (polyferric sulfate), and inorganic polymeric ferric salt composite (polymeric ferric sulfate silicate) are successfully used in clinic to treat related diseases.

Clinical Experiment I

A saturated solution of ferric subsulfate containing 0.5 wt. % toad venom was applied to surfaces of 136 tumor bodies which were located at the face, body, arms and legs of a patient suffering from senile angiomas (also called senile angiomas). The solution was then injected into the tumor bodies by using core needle penetrating into the same. The tissue structure and blood in the tumor bodies were coagulated and hardened. The tumor bodies were then softened, dehydrated and atrophied with formation of a dry eschar. It takes only 10 to 20 seconds to treat one tumor body, so that all the tumor bodies can be treated within one hour by two physicians. The eschars peeled off in the next 7 to 10 days.

Clinical Experiment II 0.25 ml of 5% polyferric sulfate was administered to a patient had varix in the anal canal (also called external hemorrhoid) by topical injection. The pathological blood vessel hardened within several seconds as a stone, and then softened in one minute. The blood vessel was dehydrated and atrophied, and become flat within 12 minutes.

Clinical Experiment III

Polyferric sulfate and polymeric ferric sulfate silicate were used as a composition for dehydrating, atrophying and eliminating pathological tissues to treat 130 patients suffering from diseases including various hemorrhoids, varix, angiomas and tumor tissues. The hemorrhoids include circumferential mixed hemorrhoids, internal hemorrhoids and external hemorrhoids. The circumferential mixed hemorrhoids are mostly acute incarcerated hemorrhoids with symptoms including different levels of infection, bleeding (blood dripping or injection bleeding), thrombus, necrosis, suppuration, aversion to cold, fever, severe pang and etc. Among these patients, some were suffered from variceal internal hemorrhoids and external hemorrhoids. Some were suffered from incarcerated hemorrhoids and had symptoms of necrosis, severe pang and fever. Some were suffered from incarcerated hemorrhoid and didn't stop bleeding because of administration of Warfarin which is used to treat coronarisms. Some were suffered from hemorrhoids that didn't stop bleeding for ten or more days and also suffered from blood-related diseases such as blood coagulation disorder and severe anemia. Some were suffered from rectal polypus or anus neoplasms. The patients are mostly senile, and one of them is a 95-year patient with hemangiomas in his anal.

The treating procedures are summarized as follows. The patient was topically disinfected, and then injected into the pathological tissues with a suitable dosage of polyferric sulfate solution containing local anaesthetics. For example, each of the hemorrhoids or tumors immediately hardened after the administration of the solution, and became soft, effused liquid, stopped bleeding and pain within one minute. The volume of the hemorrhoid was shrank to one fifth or one seventh of that prior to treatment after 10 to 30 minutes. The hemorrhoid retracted into anus. The atrophied hemorrhoid or tumor was either absorbed or peeled off after 4 to 8 days. All the patients were treated according to the same procedures and experienced the same developments without exception.

The treatment in the present invention was focused on the pathological tissues with no damages to normal tissues or physiological structures. The treating method is simple to carry out, at low cost, safe and quick. In addition, the method can be broadly used and has no significant contraindications. For example, the present method has more significant effect than conventional surgery methods such as excision, ligation, and suturing ligation, more significant effect than conventional drug injection methods such as hardener injection, necrosis agent injection, and softener injection, more significant effect than conventional physiotherapy such as electrocoagulation, laser therapy, cryotherapy, microwave therapy, low-frequency therapy, radiofrequency therapy, electric capacity field therapy, iontophoresis and electric oscillation therapy, and even more significant effect than PPH treatment (Procedure for prolapse and hemorrhoids) which is proposed and cried up by domestic and international medical community, with respect to treating hemorrhoids, varix, angiomas and topical tumor. In fact, many patients cured by the present method were previously treated by PPH operation or other conventional treatment methods.

FIGS. 2 to 12 shows the treatment effects of patient 2 to patient 12.

Figure 2F:
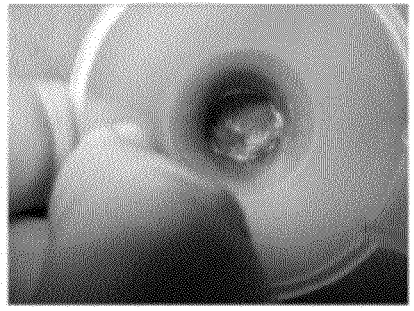
Figure 3A:
Figure 3B:
Figure 3C:
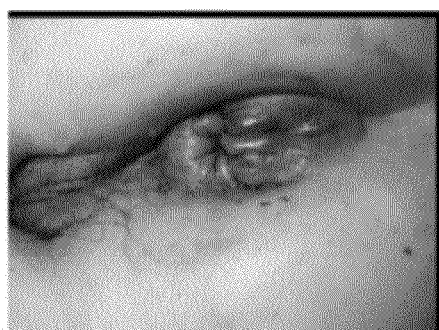
Figure 3D:
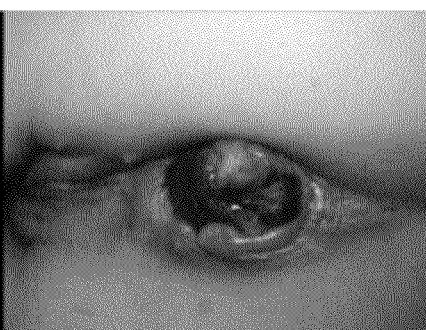
Figure 3E:
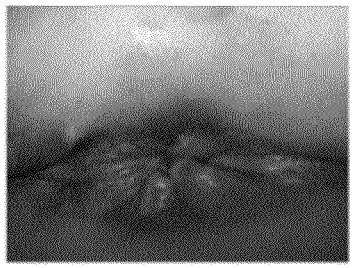
Figure 3F:
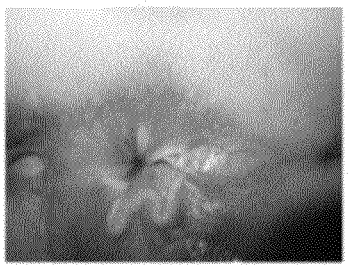
Figure 3G:
Figure 4A:
Figure 4B:
Figure 4C:
Figure 4D:
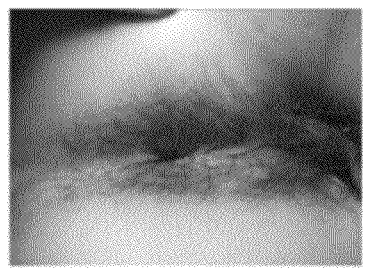

FIG. 2 shows the procedures for treating incarcerated mixed hemorrhoid. In the figures, FIG. 2A shows the topical pathological site of the patient having symptoms of necrosis, bleeding, suppurating and fever. FIG. 2B shows that the hemorrhoid is dehydrating, atrophying and eliminating during the process of injection of the drug. FIG. 2C shows the hemorrhoid is retracted into the anus 25 minutes after the injection of the drug, and endoscopy shows that the volume of the hemorrhoid is shrank to about one fifth of that before treatment. FIG. 2D shows the treatment effect 17 hours after the treatment. FIG. 2E shows the appearance of the anus 5 days after the treatment. FIG. 2F shows the observation of endoscopy 35 days after the treatment.

FIG. 3 shows the procedures for treating mixed hemorrhoid and tumor prolapsed out of anus. FIG. 3A shows the pathological site before treatment. FIG. 3B shows the tumor begins to shrink firstly 3 minutes after the injection of drug. FIG. 3C shows the tumor retracts into anus 25 minutes after the treatment. FIG. 3D shows the tumor disappears and the hemorrhoid is atrophied when the patient enforces to slip the hemorrhoid out. FIG. 3E shows the hemorrhoid retracts into anus automatically. FIG. 3F shows the pathological tissue peels off after 8 days. FIG. 3G shows the wound is almost cicatrize after 15 days.

Figure 5A:
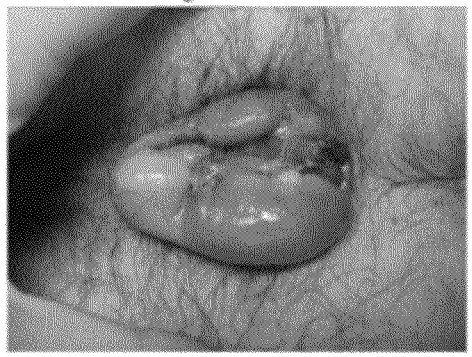
Figure 5B:
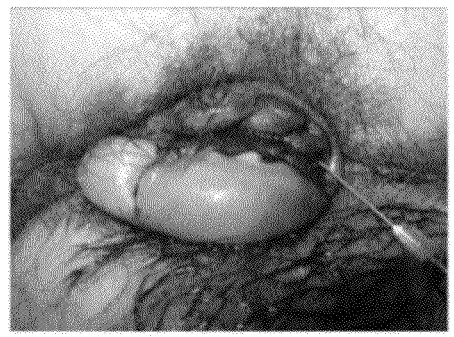
Figure 5C:
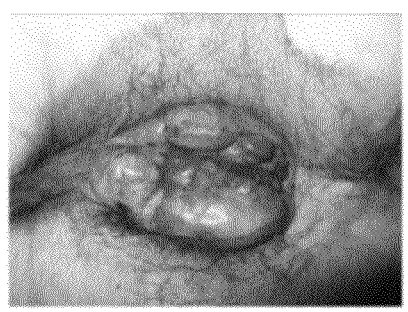
Figure 5D:
Figure 5E:
Figure 5F:
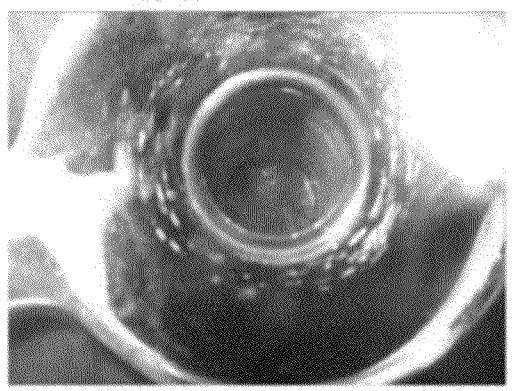
Figure 5G:
Figure 5H:
Figure 6A:
Figure 6B:
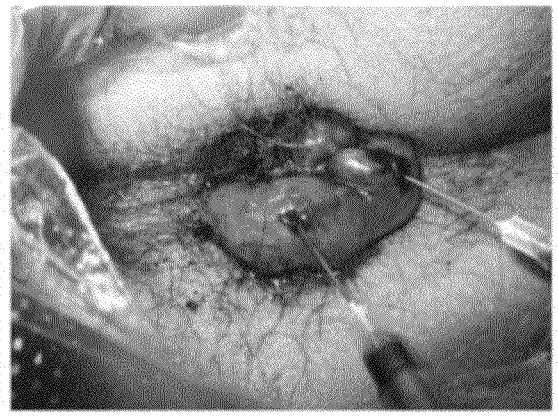
Figure 6C:
Figure 6D:
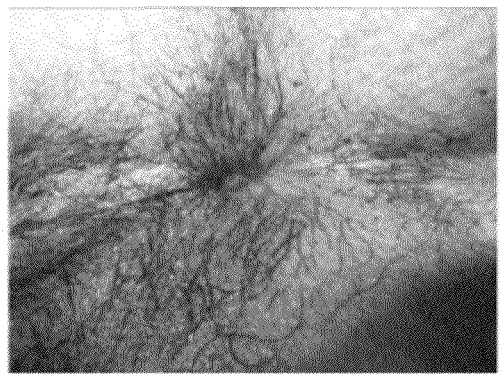
Figure 6E:
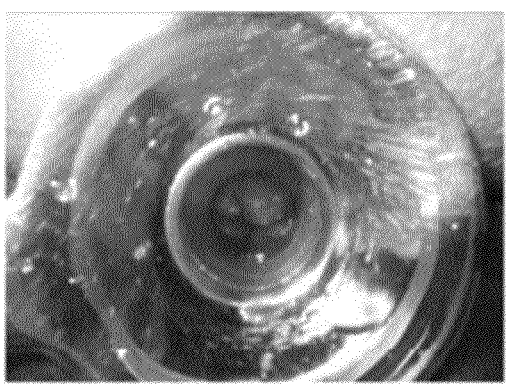
Figure 6F:
Figure 7A:
Figure 7B:
Figure 7C:
Figure 7D:
Figure 8A:
Figure 8B:
Figure 8C:
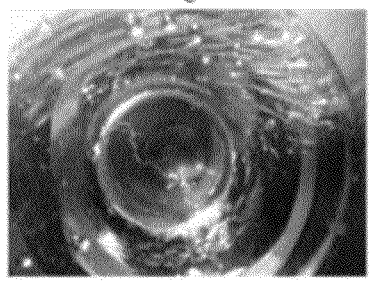
Figure 8D:
Figure 8E:
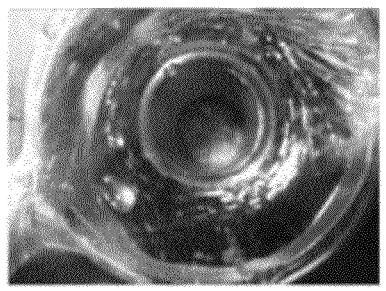
Figure 8F:
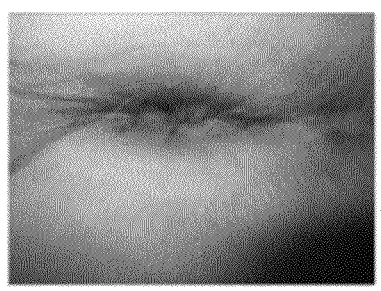
Figure 9A:
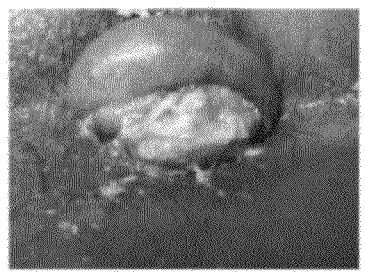
Figure 9B:
Figure 9C:
Figure 9D:
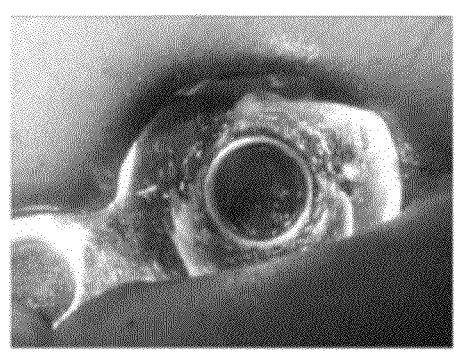
Figure 9E:
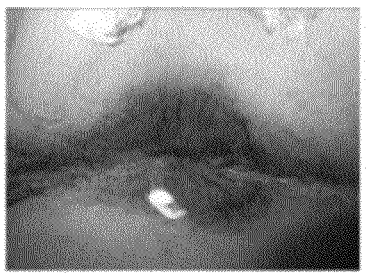
Figure 9F:
Figure 9G:
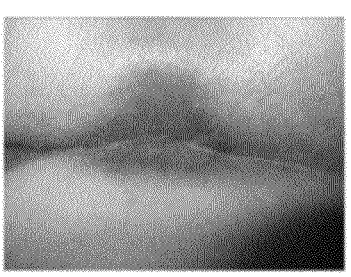
Figure 10A:
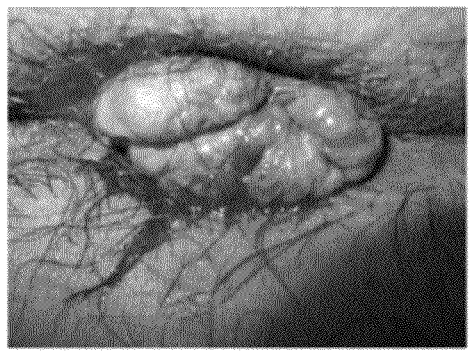
Figure 10B:
Figure 10C:
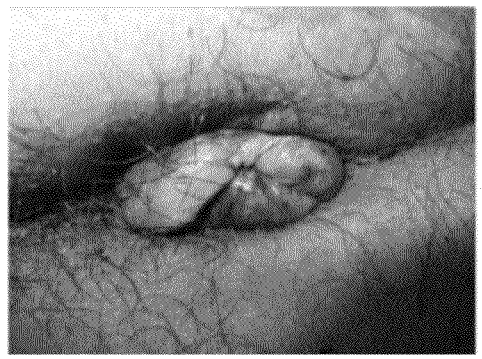
Figure 10D:
Figure 10E:
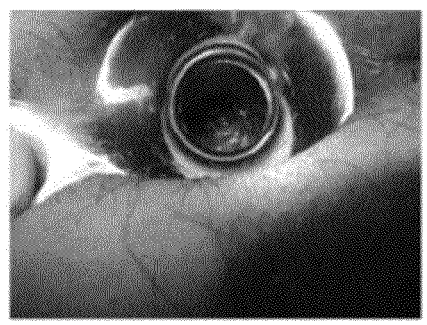
Figure 11A:
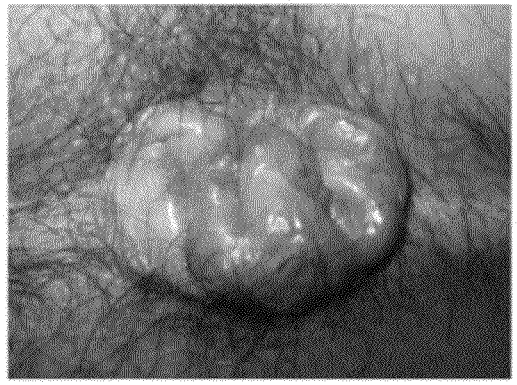
Figure 11B:
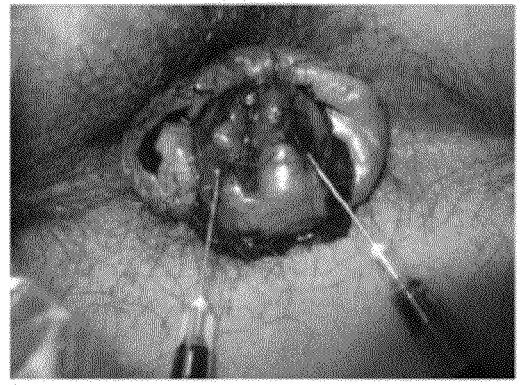
Figure 11C:
Figure 11D:
Figure 11E:
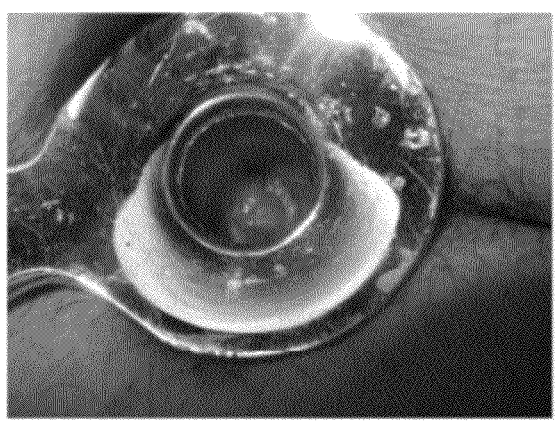
Figure 11F:
Figure 11G:
Figure 12A:
Figure 12B:
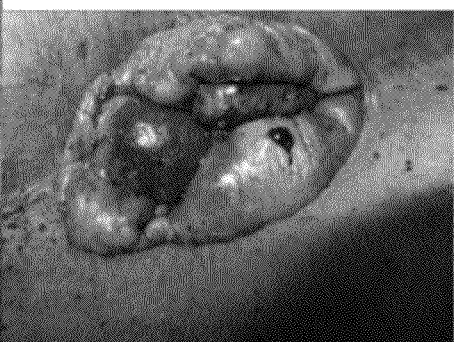
Figure 12C:
Figure 12D:
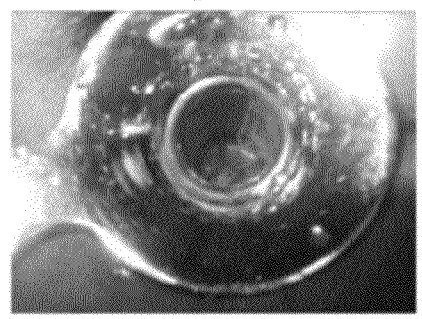
Figure 12E:
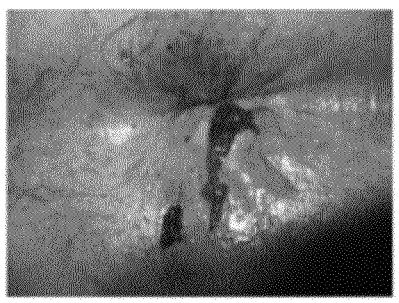
Figure 12F:
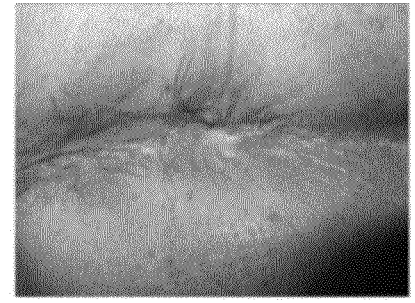
Figure 12G:
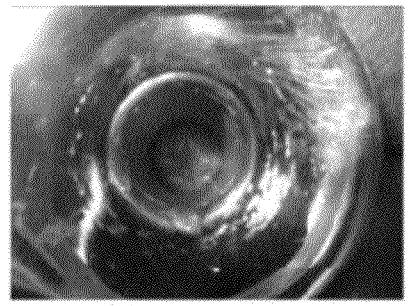

FIG. 4 shows the procedures for treating incarcerated mixed hemorrhoid that does not stop bleeding. In these figures, FIG. 4A shows the pathological site before treatment. FIG. 4B shows the injection of dehydration and atrophy drug solution. FIG. 4C shows the pathological site 10 minutes after the injection. FIG. 4D shows the pathological site 25 minutes after the injection FIG. 5 shows the procedures for treating another incarcerated mixed hemorrhoid with symptom of necrosis. In these figures, FIG. 5A shows the pathological site before treatment. FIG. 5B shows the injection of dehydration and atrophy drug solution. FIG. 5C shows the drug solution is injected completely in 5 minutes. FIG. 5D shows the pathological tissue is experiencing dehydration and atrophy 29 minutes after the injection. FIG. 5E shows the atrophied hemorrhoid retracts into anus 30 minutes after the injection. FIG. 5F shows the view observed by an anoscope 31 minutes after the injection. FIG. 5G shows the wound after the hemorrhoid is eliminated after 11 days. FIG. 5H shows the anus 41 days after the treatment.

FIG. 6 shows the procedures for treating annular varix below anal canal dentate line. In the figures, FIG. 6A shows the pathological site before treatment. FIG. 6B shows the injection of dehydration and atrophy drug solution. FIG. 6C shows the drug solution is injected completely in 7 minutes and the hemorrhoid treated earlier is atrophied. FIG. 6D shows the condition after 22 minutes. FIG. 6E shows the condition after 25 minutes. FIG. 6F shows the condition after defecation after 2 days.

FIG. 7 shows the procedure for treating a 95-year old lady who is suffered from diabetes, hypertension and apoplexy. The patient is also suffered from angioma which was prolapsed out of anus. In these figures, FIG. 7A shows the pathological site before treatment. FIG. 7B show that the tumor likes a tree with crown, leaf, fruit, bole and root, and drug is injected into the crown. FIG. 7C shows injection of drug to the bole and root to dehydrate and atrophy the same and peel off the atrophied crown. FIG. 7D shows the condition of the pathological site after 12 minutes.

FIG. 8 shows the procedure for treating a 78-year old male patient who is suffered from hypertension and taking cardiac depressants, antihypertensive agents and Warfarin for long. The patient is also suffered from tumor which is prolapsed out of anus. In these figures, FIG. 8A shows the pathological site before treatment. FIG. 8B shows the pathological site after the injection of drug. FIG. 8C shows the tumor is atrophied after 15 minutes. FIG. 8D shows the atrophied substances peel off after 11 days. FIG. 8E shows the cicatrized wound after 41 days. FIG. 8F shows the appearance of anus.

FIG. 9 shows the procedure for treating a 52-year old male patient who is suffered from pancreatic cancer. The patient is also suffered from mixed hemorrhoid and polypus incarceration with symptoms of necrosis, suppuration, and severe pain. In these figures, FIG. 9A shows the pathological site before treatment. FIG. 9B shows the hemorrhoid during injection of drug. FIG. 9C shows the drug is injected completely and the hemorrhoid is atrophying. FIG. 9D shows the atrophied hemorrhoid retracts into anus after 20 minutes with the hemorrhoid having a diameter of 1.5 cm. FIG. 9E shows that a black substances peeled off after 6 days. FIG. 9G shows the wound was healed after 21 days.

FIG. 10 shows the procedures for treating a 60-year old male patient who is suffered from incarcerated hemorrhoid. This patient was experienced coronary intervention and suffered from angina pectoris. He has been taking Warfarin for long and the hemorrhoid does not stop bleeding. In these figures, FIG. 10A shows the pathological site before treatment. FIG. 10B shows the pathological site 2 minutes after drug injection. FIG. 10C shows the hemorrhoid is dehydrated and atrophied, and stop bleeding after 5 minutes. FIG. 10D shows the hemorrhoid retracts into anus after 15 minutes. FIG. 10E shows the atrophied hemorrhoid in the anus.

FIG. 11 shows the procedures for treating a 56-year old male patient who is suffered from hemorrhoid recrudescence. The patient is also suffered from hypertension and angina pectoris, and has been taking Warfarin for long. The hemorrhoid is prolapsed after defecation and bleeding. The patient was experienced two ligation surgeries in the recent 4 years. In these figures, FIG. 11A shows the pathological site before treatment. FIG. 11B shows the pathological site after drug injection. FIG. 11C shows the hemorrhoid is dehydrated and atrophied after 5 minutes. FIG. 11D shows the hemorrhoid retracts into anus. FIG. 11E shows an internal hemorrhoid in the anus and no drug is administrated. FIG. 11F shows additional drug is injected. FIG. 11G shows the appearance of anus on day 14.

FIG. 12 shows the procedures for treating an 83-year old male patient who is suffered from hypertension and diabetes. The patient has a history of prolapsed after defecation (retractable) for 10 years. The patient is also suffered from mixed hemorrhoid, with the external hemorrhoid part be variceal and the internal hemorrhoid part experiencing erosive haemorrhage. In these figures, FIG. 12A shows the pathological site before treatment. FIG. 12B shows the pathological site after drug injection. FIG. 12C shows the hemorrhoid retracts into anus after 14 minutes. FIG. 12D shows the view observed by an anoscope. FIG. 12E shows the substances peeled off on day 5. FIG. 12F shows the pathological site on day 11. FIG. 12G shows the pathological site on day 30.

What is claimed is:

1. A method, comprising:
   administering, to a human subject in need thereof, an amount of at least one selected from the group consisting of an inorganic polymeric ferric salt and an inorganic polymeric ferric salt composite,
   wherein the amount is effective for dehydrating, atrophying and/or eliminating a pathological tissue, and
   wherein said inorganic polymeric ferric salt is polyferric sulfate, and said inorganic polymeric ferric salt composite is at least one selected from a group consisting of a poly-silicate ferric salt and a polyphosphate ferric salt.

2. The method of claim 1, wherein said poly-silicate ferric salt is at least one selected from the group consisting of polymeric ferric sulfate silicate (PFSS) and polyferric silicate chloride (PFSC), and said polyphosphate ferric salt is polyphosphate ferric sulfate (PPFS).

3. The method of claim 1, wherein the at least one selected from the group consisting of an inorganic polymeric ferric salt and an inorganic polymeric ferric salt composite is in the form of a solid powder preparation, a paste preparation, a powder injection preparation, an aqua preparation, an injection preparation, a lininment preparation for external application, a suppository preparation, or a spray preparation.

4. The method of claim 3, wherein said method further comprises administering at least one anesthetic selected from the group consisting of levobupivacaine, ropivacaine, lidocaine hydrochloride, menthol, methylene blue, procaine and tetracaine.

5. The method of claim 4, wherein said method comprises administering a solid powder preparation which contains 1~60 wt. % of inorganic polymeric ferric salt and/or inorganic polymeric ferric salt composite, adequate amount of anesthetic, and balanced amount of a pharmaceutically acceptable solid excipient.

6. The method of claim 4, wherein said method comprises administering a solid powder preparation which contains 1~60 wt. % of inorganic polymeric ferric salt and/or inorganic polymeric ferric salt composite, 40~80 wt. % of zeolite powder, and balanced amount of a pharmaceutically acceptable solid excipient.

7. The method of claim 4, wherein said method comprises administering a paste preparation which contains 1~60 wt. % of inorganic polymeric ferric salt and/or inorganic polymeric ferric salt composite, adequate amount of anesthetic, and balanced amount of a pharmaceutically acceptable excipient.

8. The method of claim 4, wherein said method comprises administering an aqua preparation which contains 0.2~60 wt. % of inorganic polymeric ferric salt and/or inorganic polymeric ferric salt composite, adequate amount of anesthetic, and balanced amount of water.

\* \* \* \* \*